United States Patent
Moses et al.

(10) Patent No.: US 8,617,607 B2
(45) Date of Patent: Dec. 31, 2013

(54) SUSTAINED RELEASE FORMULATIONS OF PSYCHOACTIVE DRUGS

(75) Inventors: Arikha Moses, New York, NY (US); Fatima Buevich, Highland Park, NJ (US); Satish Pulapura, Bridgewater, NJ (US)

(73) Assignee: TYRX, Inc., Monmouth Junction, NJ (US)

( * ) Notice: Subject to any disclaimer, the term of this patent is extended or adjusted under 35 U.S.C. 154(b) by 687 days.

(21) Appl. No.: 12/500,852

(22) Filed: Jul. 10, 2009

(65) Prior Publication Data

US 2010/0130478 A1    May 27, 2010

Related U.S. Application Data

(60) Provisional application No. 61/079,804, filed on Jul. 10, 2008.

(51) Int. Cl.
*A61K 9/14*     (2006.01)
*A61K 31/19*    (2006.01)

(52) U.S. Cl.
USPC ............................ 424/489; 514/569; 514/570

(58) Field of Classification Search
None
See application file for complete search history.

(56) References Cited

U.S. PATENT DOCUMENTS

| | | |
|---|---|---|
| 5,216,115 A | 6/1993 | Kohn et al. |
| 2004/0254334 A1 * | 12/2004 | James et al. ................. 528/310 |
| 2005/0165203 A1 | 7/2005 | Kohn et al. |
| 2006/0171990 A1 * | 8/2006 | Asgari .......................... 424/426 |
| 2007/0275027 A1 * | 11/2007 | Wen et al. ..................... 424/422 |
| 2007/0293480 A1 | 12/2007 | Seed et al. |
| 2008/0004254 A1 | 1/2008 | Barak |

OTHER PUBLICATIONS

Vivek et al. Investigations of the effect of the lipid matrix on drug entrapment, in vitro release and physical stability of olanzapine-loaded solid lipid nanoparticles. AAPS PharmSciTech, 2007, 8(4), Article 83.*

Young, "International Search Report" from PCT/US2009/050232, 2 pages, United Sates Patent and Trademark Office, Alexandria, Virginia (mailed Aug. 14, 2009).

Young, "Written Opinion of the International Searching Authority" from PCT/US2009/050232, 4 pages, United Sates Patent and Trademark Office, Alexandria, Virginia (mailed Aug. 14, 2009).

\* cited by examiner

*Primary Examiner* — Anna Pagonakis
(74) *Attorney, Agent, or Firm* — Lerner, David, Littenberg, Krumholz & Mentlik, LLP

(57) ABSTRACT

This invention provides biodegradable, sustained-release pharmaceutical compositions of a psychoactive drug formulated with biocompatible, biodegradable tyrosine-derived polyarylates.

25 Claims, 6 Drawing Sheets

SUSTAINED RELEASE FORMULATIONS OF PSYCHOACTIVE DRUGS

RELATED APPLICATION

This application claims the benefit of and priority to U.S. provisional application Ser. No. 61/079,804 filed Jul. 10, 2008 in the U.S. Patent and Trademark office, which is hereby incorporated by reference herein in its entirety.

FIELD OF THE INVENTION

This invention provides biodegradable, sustained-release pharmaceutical compositions of a psychoactive drug formulated with biocompatible, biodegradable tyrosine-derived polyarylates.

BACKGROUND

Psychoactive drugs (e.g., typical psychoactives and atypical psychoactives) are used to help manage symptoms of schizophrenia, the manic phase of manic depression, and other psychotic disorders. These drugs are typically available in several formulations: oral tablets, dissolving tablets, and intramuscular injection. One significant side effect of psychoactive drugs is weight gain (Wirshing D A, Wirshing W C, Kysar L, Berisford M A. (1999) Novel psychoactives: comparison of weight gain liabilities. *Journal of Clinical Psychology* 60 358-63) especially at high doses (Green B (1999) Focus on olanzapine *Current Med Res Opin* 15 79-85).

Patient compliance is of vital importance in conditions such as schizophrenia for which psychoactive drugs find utility. It is often observed that patients refuse to take oral medication for reasons associated with the symptoms of their condition. To improve patient compliance, it would be beneficial to develop a controlled release formulation of an psychoactive drug that provides steady therapeutically useful plasma levels of drug over a sustained period of time.

SUMMARY

The invention provides sustained-release and burst-free sustained-release formulations of a psychopharmacologic agent using a family of resorbable tyrosine derived polyarylates. Those polymers have a wide variety of resorption times and a known history of safety and efficacy as coatings on medical devices. In compositions of the present invention, a polymer matrix is formed by a biodegradable polyarylate polymer in which a drug or combination of drugs is dispersed, dissolved, or embedded in the matrix.

Release of the drug from the polymer matrix may be by diffusion, degradation of the polyarylate polymer, or a combination of both mechanisms. When drug diffuses from the polymer matrix, the polyarylate remains mostly intact until most or all of the drug is released. In the case of a degradative mechanism of release, drug is released from the polymer matrix as the polymer matrix erodes. Whether drug release is by diffusion or degradation is determined by the selection of polymeric materials as provided herein. It is also contemplated that drug release can be partly by diffusion and partly by degradation. This provides useful flexibility, allowing for the production of compositions that exhibit complicated, multiphasic release patterns, if such is desired.

When compositions of the present invention are formulated as microparticles, even more flexibility is provided. Microparticles can be mixed by size or by type of polymer, preferably a polyarylate. Microparticles containing different drugs can also be mixed. This variety can provide for the delivery of drugs to the patient in a multiphasic manner and/or in a manner that provides different drugs to the patient at different times, or a mixture of more than one drug at the same time. One can even mix different drug types in the same composition. For example, antibiotics, vaccines, angiogenic agents, cytokines, or any desired active agent, can be provided to the patient.

An aspect of the invention provides a sustained-release formulation comprising an psychoactive drug and a tyrosine-derived polyarylate. Another aspect of the invention provides a burst-free, sustained-release formulation including an psychoactive and a tyrosine-derived polyarylate. The psychoactive drug can be a typical psychoactive drug or an atypical psychoactive drug. In certain embodiments, when measured in vitro under physiological conditions at 37° C., amounts are such that these formulations release the psychoactive for at least 1 to 5 days. In other embodiments, sustained drug delivery for even longer periods is possible. The physiological conditions are in phosphate buffered saline (PBS). In certain embodiments, the formulation includes an amount of psychoactive ranging from about 10% to about 40% by weight.

An exemplary atypical psychoactive is olanzapine. The polyarylate can be a poly(DT-DTE succinate) or a poly(DTE succinate), in which, DT, when present ranges from about 5% to about 50%, from about 5% to about 30%, from about 10% to about 20% of the polyarylate or is about 5%. 10%. 15%. 20%, 25% or 30% of said polyarylate. The polyarylate can also be poly(10% DT-DTE adipate), poly(10% DT-DTE succinate), poly(10% DT-DTE succinate) of low molecular weight, poly(10% DT-DTE succinate) of high molecular weight, poly(10% DT-DTO adipate) or poly(10% DT-DTO sebacate).

A preferred polyarylate for use in the present invention can be represented by Formula 1

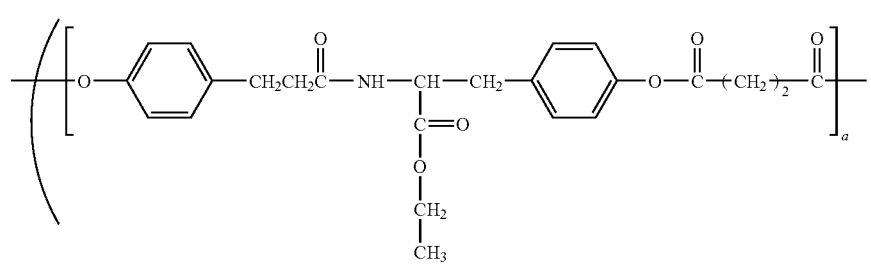

Formula 1

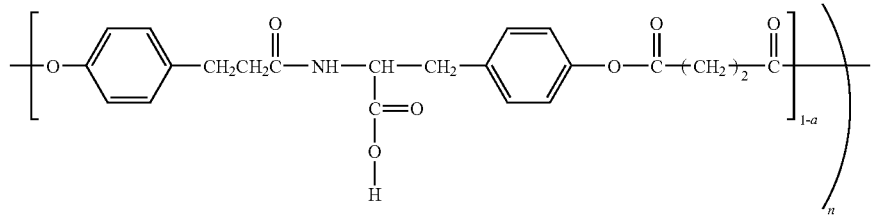

where a is a number between 0.01 and 0.99 that represents the mole fraction of esters in the pendant chains of the polyarylate as compared to the mole fraction of free carboxylic acid groups in the pendant chains. Preferred values of a are: between about 0.50 and about 0.98; between about 0.80 and about 0.97; between about 0.80 and about 0.95; between about 0.85 and about 0.95; and between about 0.90 and about 0.95, Also among the preferred values of a are: about 0.95, about 0.90, about 0.85, about 0.80, about 0.75, about 0.70, and about 0.60.

The formulation can be prepared by a method selected from the group consisting of a solvent-cast film method, a solvent-free film method, microparticle method, and microsphere method.

Another aspect of the invention provides a method of treating a psychiatric condition in a subject including administering a sustained-release or burst-free sustained-release formulation including an psychoactive and a tyrosine-derived polyarylate. An exemplary psychiatric condition is schizophrenia.

DETAILED DESCRIPTION

Figure 1:
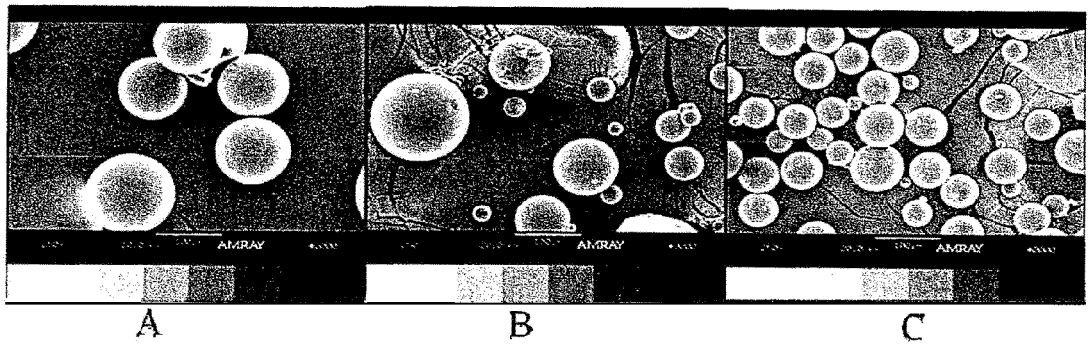
FIG. 1 is a set of photographs showing spherical particles of the polymer family of polyarylates.

In compositions of the present invention, a polymer matrix is formed by a biodegradable polyarylate polymer in which a drug, preferably a psychoactive drug, is dispersed, dissolved, or embedded in the matrix. The psychoactive drug is released over a sustained period of time. Embodiments of the invention are formulated as sustained-release formulations and burst-free sustained-release formulations.

Sustained release refers to a formulation in which release of the psychoactive drug occurs for at least 1-5 days and for as long as 2-4 months, depending on the choice of psychoactive drug, polymer, relative amounts of the psychoactive drug and the polymer, and the physical form of the formulation (e.g., microparticles, microspheres, etc.). To determine if sustained release has occurred, the release profile of the psychoactive drug is measured in vitro in phosphate buffered saline at 37° C. The measurement can also be done in vitro under general physiological conditions 37° C.

The present invention provides drug delivery devices including a polyarylate matrix and an psychoactive drug dispersed therein where not more than about 1%, about 2%, about 3%, about 4%, about 5%, about 6%, about 7%, about 8%, or about 9% of the psychoactive drug is released within the first 24 hours after implantation. The present invention provides drug delivery devices comprising a polyarylate matrix and an psychoactive drug dispersed therein where not more than about 2%, about 3%, about 4%, about 5%, about 6%, about 7%, about 8%, about 9%, about 10%, about 11%, about 12%, about 13%, about 14%, about 15%, about 16%, about 17%, about 18%, or about 19% of the psychoactive drug is released within the first 24 hours after implantation.

A burst-free sustained-release formulation refers to a formulation in which less than about 50% of the psychoactive drug is released within 24 hours. To determine if burst-free release has occurred, the release profile of the psychoactive drug is measured in vitro in phosphate buffered saline at 37° C. The measurement can also be done in vivo under general physiological conditions at 37° C. The in vitro determined release correlates with and is representative of effective burst-free, sustained-released compositions with desirable in vivo efficacy.

Polymers

Polyarylates are alternating A-B type copolymers consisting of a diphenol component and a dicarboxylic acid component. The dicarboxylic acids allow for variation in the polymer backbone while the diphenols contain a moiety for appending and varying a pendent chain. The present invention employs certain polyarylates in which an psychoactive drug has been dispersed, dissolved, or embedded for medical applications. The polyarylates are based upon certain tyrosine-derived monomers, which are co-polymerized with a variety of dicarboxylic acids. The tyrosine-derived monomer can be thought of as a desaminotyrosyl tyrosine dipeptide in which the tyrosine moiety's pendant carboxyl group has been esterified. The structure of one example of a suitable tyrosine-derived monomer is shown in Formula 2.

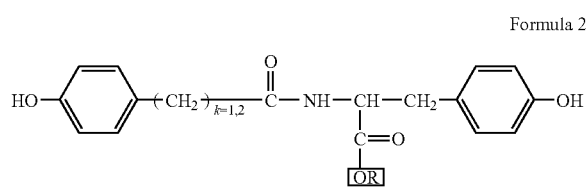

Formula 2

In Formula 2, R is selected from the group consisting of: a straight or branched chain alkyl group containing up to 18 carbon atoms, an alkylaryl group containing up to 18 carbon atoms, a straight or branched chain alkyl group containing up to 18 carbon atoms in which one or more carbon atoms is substituted by an oxygen, and an alkylaryl group containing up to 18 carbon atoms in which one or more carbon atoms is substituted by an oxygen.

In preferred embodiments, R is a straight or branched chain alkyl group containing 2-8 carbon atoms. In particular embodiments, R is selected from the group consisting of: methyl, ethyl, propyl, butyl, isobutyl, sec-butyl, hexyl, octyl, 2-(2-ethoxyethoxy)ethanyl, dodecanyl, and benzyl. In preferred embodiments, R is selected from the group consisting of: ethyl, hexyl, and octyl. In an especially preferred embodiment, R is ethyl and k is 2.

One class of polyarylates suitable for use in the present invention is formed by polymerizing the tyrosine-derived monomers of Formula 2 with the diacarboxylic acids of Formula 3.

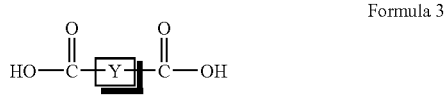

Formula 3

In Formula 3, Y is a saturated or unsaturated, substituted or unsubstituted alkylene, arylene, and alkylarylene group containing up to 18 carbon atoms. The substituted alkylene, arylene, and alkylarylene groups may have backbone carbon atoms replaced by N, O, or S, or may have backbone carbon atoms replaced by keto, amide, or ester linkages. Y is preferably selected so that the dicarboxylic acids are either important naturally-occurring metabolites or highly biocompatible compounds. Preferred dicarboxylic acids therefore include the intermediate dicarboxylic acids of the cellular respiration pathway known as the Krebs Cycle. These dicarboxylic acids include α-ketoglutaric acid, succinic acid, fumaric acid, malic acid and oxaloacetic acid, for which Y is —CH2-CH2-C(=O)—, —CH2-CH2-, —CH=CH—, —CH2-CH(—OH)—, and —CH2-C(=O)—, respectively.

In particular embodiments, Y in Formula 3 is a straight chain alkylene group having 2-8 carbons. In particular embodiments, Formula 3 is one of the following dicarboxylic acid, namely succinic acid, glutaric acid, diglycolic acid, adipic acid, 3-methyladipic acid, suberic acid, dioxaoctadioic acid and sebacic acid. Preferred dicarboxylic acids are succinic acid and adipic acid.

When polymerized, the tyrosine-derived monomers of Formula 2 and the dicarboxylic acids of Formula 3 give rise to polyarylates that can be represented by Formula 4.

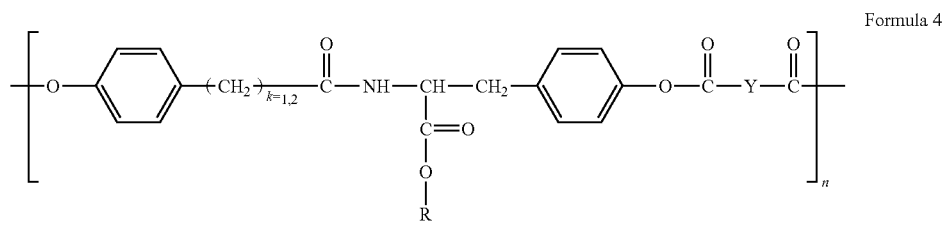

Formula 4 where R and Y are as described above. In this formula, as in other formulas herein, an "n" outside brackets or parentheses, and having no specified value, has its conventional role in the depiction of polymer structures. That is, n represents a large number, the exact number depending on the molecular weight of the polymer. This molecular weight will vary depending upon the conditions of formation of the polymer.

A preferred subset of the polyarylates of Formula 4 is the subset where k=2 and both R and Y are straight chain alkyl groups. This polyarylate subset can be represented by Formula 5.

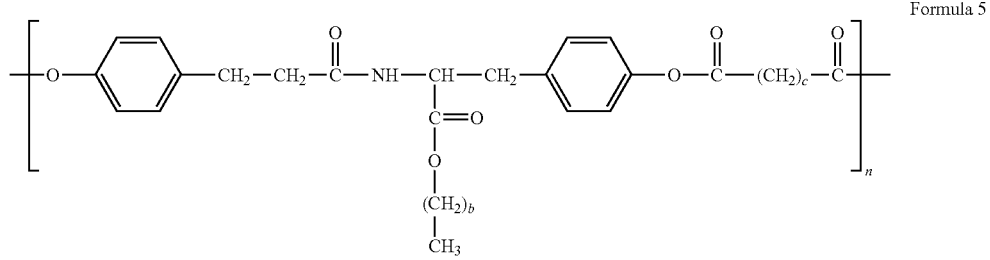

Formula 5

In Formula 5, b=1-17 and c=1-18. In preferred embodiments, b=1-7 and c=2preferred polyarylate for use in the present invention is the polyarylate of Formula 5 where b=1 and c=2. This polyarylate is referred to herein as p(DTE succinate). This name illustrates the nomenclature used herein, in which the names of polyarylates are based on the monomers making up the polyarylates. The "p" stands for polymer; the "DTE" stands for Desaminotyrosyl Tyrosine Ethyl ester; the "succinate" refers to the identity of the dicarboxylic acid. p(DTE succinate) is formed by the polymerization of the tyrosine-derived monomer desaminotyrosyl tyrosine ethyl ester and the dicarboxylic acid succinic acid.

Another preferred polyarylate for use in the present invention contains three monomer subunits: desaminotyrosyl tyrosine ethyl ester, succinic acid, and desaminotyrosyl tyrosine. The monomer desaminotyrosyl tyrosine (referred to herein as "DT") is the same as desaminotyrosyl tyrosine ethyl ester except that it contains a pendant free carboxylic acid group rather than the pendant ethyl ester of desaminotyrosyl tyrosine ethyl ester.

The inclusion of a certain percentage of desaminotyrosyl tyrosine monomers in the polymer produces a polyarylate with that certain percentage of free carboxylic acid groups in the pendant chains. The structure of the polyarylate corresponding to p(DTE succinate) but having free carboxylic acid groups in the pendant chains can be represented by Formula 1.

polyarylate generally will be random, although the overall ratio in which these two monomers appear will be governed by the value of a. Preferred values of a are: 0.97, 0.96, 0.95, 0.94, 0.93, 0.92, 0.91, 0.90, 0.89, 0.88, 0.87, 0.86, 0.85, 0.84, 0.83, 0.82, 0.81, and 0.80, 0.75, 0.70, 0.65, 0.60 and 0.55. Ranges for "a" also include 0.95-0.60, 0.90-0.70, and 0.95-0.75

The presence of free carboxylic acid groups and their percentage is indicated in the nomenclature used herein by modifying the name of the polyarylate in the manner illustrated for p(DTE succinate) as follows: p(5% DT, DTE succinate) indicates p(DTE succinate) with 5% free carboxylic acid groups, p(10% DT, DTE succinate) indicates p(DTE succinate) with 10% free carboxylic acid groups, p(15% DT, DTE succinate) indicates p(DTE succinate) with 15% free carboxylic acid groups, etc.

Another preferred polyarylate for use in the present invention is p(DTE adipate). p(DTE adipate) is formed by the polymerization of the tyrosine-derived monomer desaminotyrosyl tyrosine ethyl ester and adipic acid. Also preferred is p(DTE adipate) in which some of the pendant groups are free carboxylic acid groups, e.g., p(10% DT, DTE adipate), p(15% DT, DTE adipate), etc.

Formula 1

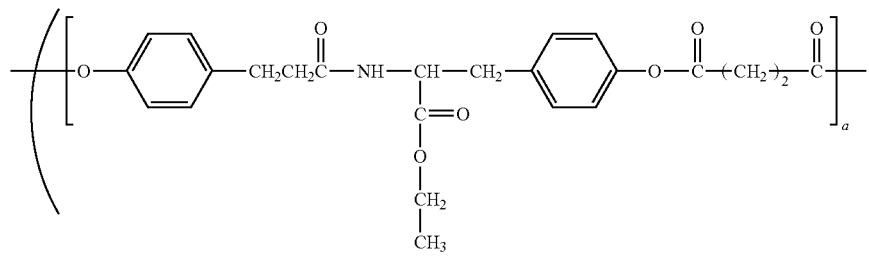

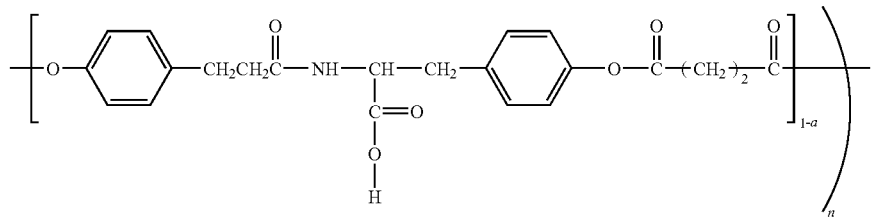

In Formula 1, or for any polymer having tyrosine-derived diphenol free acid moieties and tyrosine-derived diphenol ester moieties, a is a number between 0.01 and 0.99 that represents the mole fraction of tyrosine-derived monomer that is esterified, i.e., without a free carboxylic acid group. It is understood that the depiction of the tyrosine-derived monomers without and with free carboxylic acid groups as alternating in Formula 1 is for the sake of convenience only. Actually, the order in which tyrosine-derived monomers without free carboxylic acid groups and tyrosine-derived monomers with free carboxylic acid groups appear in the In general, any of the polyarylates employed in the present invention can contain any desired percentage of pendant groups having free carboxylic acid groups. Thus, the present invention includes compositions of matter in which an psychoactive drug is embedded, dispersed, or dissolved in a polyarylate polymer matrix where the polyarylate polymer has the structure shown in Formulas 4 or 5 except that a certain percentage of the pendant chains are free carboxylic acid groups rather than esters. The structure of the polyarylate polymer similar to Formula 4, but having free carboxylic acid groups in the pendant chains is shown in Formula 6.

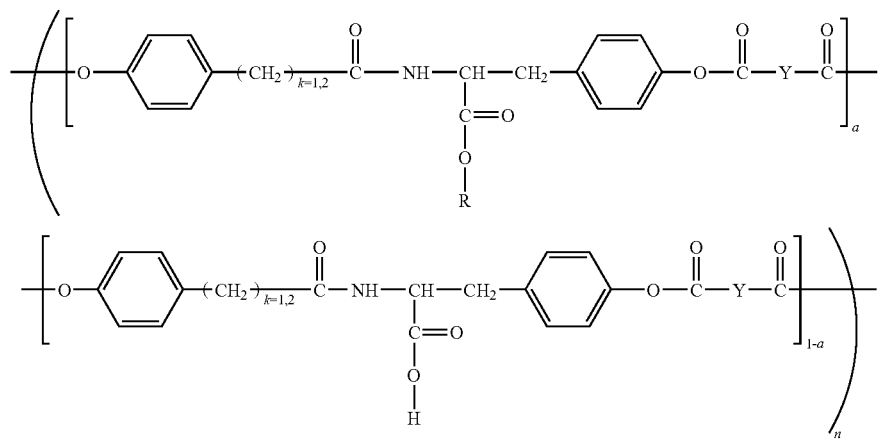

Formula 6

In Formula 6, R and Y are as in Formula 4. Usually, both instances of Y will be the same but this does not have to be the case. a is as defined above for Formula 1.

The structure of the polyarylate polymer similar to Formula 5, but having free carboxylic acid groups in the pendant chains can be represented by Formula 7.

boxylic acid groups are stable and water insoluble in acidic environments but dissolve or degrade rapidly when exposed to neutral or basic environments. By contrast, copolymers of low acid to ester ratios are more hydrophobic and will not degrade or resorb rapidly in either basic or acidic environments.

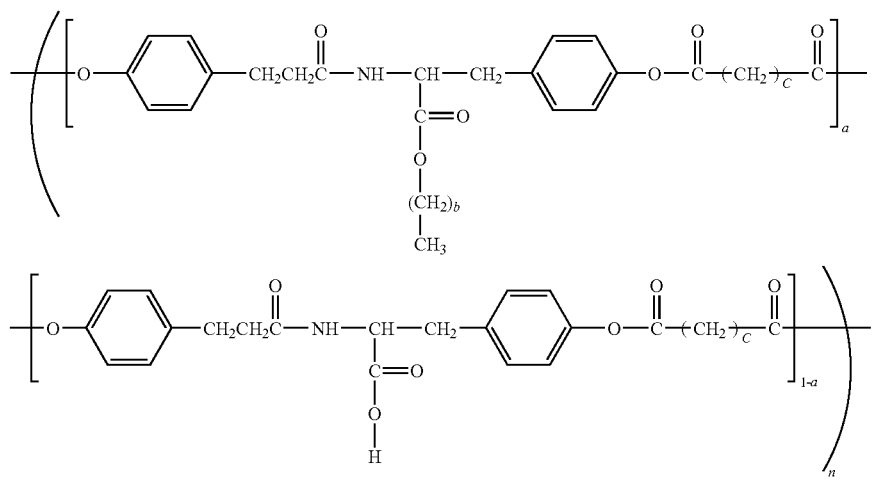

Formula 7

In Formula 7, b and c are as in Formula 5. Usually, both instances of c will be the same. Preferred values of b are 1, 5, and 7; preferred values of c are 2, 4, 6, and 8. a is as defined in Formula 1.

The incorporation of free carboxylic acid groups in the polyarylates has the effect of accelerating the rate of polymer degradation and resorption when the polyarylates are placed in physiological conditions. Physiological conditions refers to the conditions of temperature, pressure, ionic strength, and salt composition found in the mammalian body or to in vitro systems designed to mimic relevant features of those conditions such as, e.g., the phosphate buffered saline solutions used in the Examples described herein that measured release rates of psychoactive drugs.

The presence of the free carboxylic acid groups also affects the behavior of the polyarylate in response to pH. Polyarylates having a relatively high concentration of pendent car- Such characteristics imparted by the carboxylic acid groups allow for the production of drug delivery devices comprising polyarylates and psychoactive drugs that are tailored to degrade or be resorbed at predetermined rates, and to deliver predetermined amounts of psychoactive drug at predetermined rates, by choosing the proper percentage of carboxylic acid groups in the polyarylate. In particular embodiments, the percentage of pendant chains that are free carboxyl groups in the polyarylate polymers used in the present invention is about 1-99%, 5-95%, 10-80%, 15-75%, 20-50%, or 25-40%. In particular embodiments, the percentage of pendant chains that are free carboxyl groups is about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25%.

Further polymers that can be used in the present invention are co-polymers of the tyrosine-based polyarylates described above and poly(alkylene oxides). Such co-polymers are described, e.g., in U.S. Patent Ser. No. 60/375,846 and U.S. Pat. Nos. 5,658,995, and 6,120,491, the disclosures of which are incorporated by reference herein. These co-polymers are random block copolymers of a dicarboxylic acid with a tyrosine-derived diphenol and a poly(alkylene oxide), wherein an equimolar combined quantity of the diphenol and the poly(alkylene oxide) is reacted with the dicarboxylic acid in a molar ratio of the diphenol to the poly(alkylene oxide) between about 1:99 and about 99:1 to give a polymer having the following structure

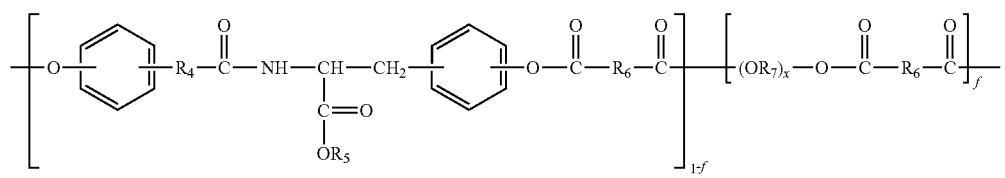

Formula 8 where $R_4$ is —CH=CH— or (—CH$_2$—)$_j$ in which j is between 0 and 8, inclusive; R5 is selected from the group consisting of straight and branched alkyl and alkylaryl groups containing up to 18 carbon atoms and optionally containing at least 1 ether linkage; R6 is selected from the group consisting of saturated and unsaturated, substituted and unsubstituted alkylene, arylene and alkylarylene groups containing up to 18 carbon atoms; each R7 is independently an alkylene group containing up to 4 carbon atoms; x is between about 5 and about 3,000; and f is the percent molar fraction of alkylene oxide in the copolymer and ranges between about 1 and about 99 mole percent.

In preferred embodiments, R4 is ethylene; R5 is ethyl; R6 is ethylene or butylene; R7 is ethylene; and all substituents on the benzene rings in the polymer backbone are in the para position.

The poly(alkylene oxide) monomer used to produce the polymer shown in Formula 8 can be any commonly used alkylene oxide known in the art, and is preferably a poly (ethylene oxide), polypropylene oxide), or poly(tetramethylene oxide). Poly(alkylene oxide) blocks containing ethylene oxide, propylene oxide or tetramethylene oxide units in various combinations are also possible constituents within the context of the current invention.

The poly(alkylene oxide) is most preferably a poly(ethylene oxide) in which x of Formula 8 is between about 10 and about 500, or about 20 and about 200. In certain embodiments, poly(ethylene oxide) blocks with a molecular weight of about 1,000 to about 20,000 g/mol are used.

While many biodegradable tyrosine-derived polyarylates are specifically illustrated above, further such polymers for use in the invention are described in U.S. Pat. Nos. 5,099,060; 5,216,115; 5,317,077; 5,587,507; 5,658,995; 5,670,602; 6,048,521; 6,120,491; 6,319,492; 6,475,477; 6,602,497; 6,852,308; 7,056,493; RE37,160E; and RE37,795E; as well as those described in U.S. Patent Application Publication Nos. 2002/0151668; 2003/0138488; 2003/0216307; 2004/0254334; 2005/0165203; and those described in PCT Publication Nos. WO99/52962; WO 01/49249; WO 01/49311; WO03/091337.

The tyrosine-derived diphenol compounds used to produce the polyarylates suitable for use in the present invention can be produced by known methods such as those described in, e.g., U.S. Pat. Nos. 5,099,060 and 5,216,115, the disclosures of which are incorporated by reference herein. The production of desaminotyrosyl tyrosine ethyl ester, desaminotyrosyl tyrosine hexyl ester, and desaminotyrosyl tyrosine octyl ester can also be carried out by known methods, see, e.g., Pulapura & Kohn, 1992, Biopolymers 32:411-417 and Pulapura et al., 1990, Biomaterials 11:666-678.

The dicarboxylic acids are widely available from a variety of commercial sources. A tyrosine-derived diphenol monomer and a dicarboxylic acid may be reacted to form a polyarylate suitable for use in the present invention according to the methods disclosed in U.S. Pat. No. 5,216,115, the disclosures of which are incorporated by reference herein. According to these methods, the diphenol compounds are reacted with the dicarboxylic acids in a carbodiimide-mediated direct polyesterification using 4-(dimethylamino)pyridinium-p-toluene sulfonate (DPTS) as a catalyst to form the polyarylates. Random block copolymers with poly(alkylene oxide) according to Formula 8 may be formed by substituting poly (alkylene oxide) for the tyrosine derived diphenol compound in an amount effective to provide the desired ratio of diphenol to poly(alkylene oxide) in the random block copolymer.

C-terminus protected alkyl and alkylaryl esters of tyrosine containing up to 8 carbon atoms can be prepared according to the procedure disclosed in J. P. Greenstein and M. Winitz, Chemistry of the Amino Acids, (John Wiley & Sons, New York 1961), p. 929. C-terminus protected alkyl and alkylaryl esters of tyrosine containing more than 8 carbon atoms can be prepared according to the procedure disclosed in U.S. Pat. No. 4,428,932.

N-terminus protected tyrosines can be prepared following standard procedures of peptide chemistry such as disclosed in Bodanszky, Practice of Peptide Synthesis (Springer-Verlag, New York, 1984).

The crude tyrosine derivatives are sometimes obtained as oils and can be purified by simple recrystallization. Crystallization of the pure product is accelerated by crystal seeding. The diphenols can then be prepared by carbodiimide-mediated coupling reactions in the presence of hydroxybenzotriazide following standard procedures of peptide chemistry such as disclosed in Bodanszky, Practice of Peptide Synthesis (Springer-Verlag, New York, 1984) at page 145. The crude diphenols can be recrystallized twice, first from 50% acetic acid and water and then from a 20:20:1 ratio of ethyl acetate, hexane, and methanol, or, alternatively, by flash chromatography on silica gel, employing a 100:2 mixture of methylene chloride:methanol as the mobile phase. Desaminotyrosyl tyrosine esters also can be prepared by the carbodiimide mediated coupling of desaminotyrosine and tyrosine esters in the presence of hydroxybenzotriazole.

The diphenol compounds can then be reacted with dicarboxylic acids in a carbodiimide-mediated direct polyesterification using 4-(dimethylamino)pyridinium-p-toluene sulfonate (DPTS) as a catalyst to form polyarylates.

Because the diphenols of the present invention are base-sensitive, the polyarylates of the present invention are prepared by direct polyesterification, rather than by dicarboxylic acid chloride techniques. Polyesterification condensing agents and reaction conditions should be chosen that are compatible with the base-sensitive diphenol starting materials. Thus, the polyarylates can also be prepared by the process disclosed by Ogata et al., 1981, Polym. J., 13:989-991 and Yasuda et al., 1983, J. Polym. Sci: Polym. Chem. Ed., 21:2609-2616 using triphenylphosphine as the condensing agent; the process of Tanaka et al., 1982, Polym. J. 14:643-648 using picryl chloride as the condensing agent; or by the process of Higashi et al., 1986, J. Polym. Sci: Polym. Chem. Ed. 24:589-594 using phosphorus oxychloride as the condensing agent with lithium chloride monohydrate as a catalyst.

The polyarylates can also be prepared by the method disclosed by Higashi et al., 1983, J. Polym. Sci.: Polym. Chem. Ed. 21:3233-3239 using arylsulfonyl chloride as the condensing agent; by the process of Higashi et al., 1983, J. Polym. Sci.: Polym. Chem. Ed. 21:3241-3247 using diphenyl chlorophosphate as the condensing agent; by the process of Higashi et al., 1986, J. Polym. Sci.: Polym. Chem. Ed. 24:97-102 using thionyl chloride with pyridine as the condensing agent; or by the process of Elias, et al., 1981, Makromol. Chem. 182:681-686 using thionyl chloride with triethylamine. An additional polyesterification procedure is the method disclosed by Moore et al., 1990, Macromol. 23:65-70 utilizing carbodiimide coupling reagents as the condensing agents with the specially designed catalyst 4-(dimethylamino)pyridinium-p-toluene sulfonate (DPTS). A particular polyesterification technique modifies the method of Moore to utilize an excess of the carbodiimide coupling reagent. This produces aliphatic polyarylates having molecular weights greater than those obtained by Moore. When carbodiimides are used in peptide synthesis as disclosed by Bodanszky, Practice of Peptide Synthesis (Springer-Verlag, New York, 1984), between 0.5 to 1.0 molar equivalents of carbodiimide reagent is used for each mole of carboxylic acid group present. In the preferred methods disclosed herein, greater than 1.0 molar equivalents of carbodiimide per mole of carboxylic acid group present are used. This is what is meant by describing the reaction mixture as containing an excess of carbodiiide.

Essentially any carbodiimide commonly used as a coupling reagent in peptide chemistry can be used as a condensing agent in the preferred polyesterification process. Such carbodiimides are well-known and disclosed in Bodanszky, Practice of Peptide Synthesis (Springer-Verlag, New York, 1984) and include dicyclohexylcarbodiimide, diisopropylcarbodiimide, 1-(3-dimethylaminopropyl)-3-ethyl carbodiimide hydrochloride, N-cyclohexyl-N'-(2'-morpholinoethyl) carbodiimide-metho-p-toluene sulfonate, N-benzyl-N'-3'-dimethylaminopropyl-carbodiimide hydrochloride, 1-ethyl-3-(3-dimethylaminopropyl)carbodiimide methiodide, N-ethylcarbodiimide hydrochloride, and the like. The preferred carbodiimides are dicyclohexyl carbodiimide and diisopropylcarbodiimide.

A reaction mixture is formed by contacting equimolar quantities of the diphenol and the dicarboxylic acid in a solvent for the diphenol and the dicarboxylic acid. Suitable solvents include methylene chloride, tetrahydrofuran, dimethylformamide, chloroform, carbon tetrachloride, and N-methyl pyrrolidinone. It is not necessary to bring all reagents into complete solution prior to initiating the polyesterification reaction, although the polymerization of slightly soluble monomers such as desaminotyrosyl tyrosine ethyl ester and succinic acid will yield higher molecular weight polymers when the amount of solvent is increased. The reaction mixture can also be heated gently to aid in the partial dissolution of the reactants.

The polymer molecular weight significantly increases as the amount of coupling reagent used is increased. The degree of molecular weight increase only begins to level off around four molar equivalents of carbodiimide per mole of carboxylic acid group. Increasing the amount of coupling reagent beyond four equivalents of carbodiimide has no further beneficial effect. While quantities of carbodiimide greater than four equivalents are not detrimental to the polyesterification reaction, such quantities are not cost-effective and are thus not favored for this reason.

Carbodiimide-mediated direct polyesterification can be performed in the presence of the catalyst 4-(dimethylamino) pyridinium-p-toluene sulfonate (DPTS). DPTS is prepared in accordance with the procedure of Moore et al., 1990, Macromol., 23:65-70. The amount of DPTS is not critical because the material is a true catalyst that is regenerated. The catalytically effective quantity is generally between about 0.1 and about 2.0 molar equivalents per mole of carboxylic acid group, and preferably about 0.5 equivalents per mole of carboxylic acid group. The reaction proceeds at room temperature, or about 20-30° C. The reaction mixture can be heated slightly (<60° C.) prior to carbodiimide addition to partially solubilize less soluble monomers. However, the polymerization reaction itself should be conducted between 20° C. and 30° C. Within this temperature range, the reaction can be continued, with stirring, for at least 12 hours, and preferably for from one to four days. The polymer is recovered by quenching the reaction mixture in methanol, from which the polyarylate usually precipitates while the residual reagents remain in solution. The precipitate may be separated by mechanical separations such as filtration and purified by solvent washing.

In a preferred procedure, equimolar amounts of pure, dried tyrosine-derived diphenol and dicarboxylic acid are weighed and placed in a round-bottomed flask, pre-dried at 130° C. A suitable magnetic stir bar is placed into the flask. Then 0.4 equivalents of DPTS are added. The flask is fitted with a septum and flushed with nitrogen or argon to remove traces of moisture from the reaction mixture. Next, a quantity of HPLC grade methylene chloride is added via a syringe and the reaction mixture is stirred vigorously to suspend the reactants. The amount of methylene chloride used will depend upon the solubility of the diphenol, or the dicarboxylic acid, or both monomers. At this stage, the reaction mixture may be slightly heated to partially dissolve the monomers. While it is not essential that the monomers be completely dissolved, the quantity of solvent should be sufficient to dissolve the polymer as it forms and thus slowly bring the monomers into solution.

4.0 equivalents of diisopropylcarbodiimide are then added to the reaction mixture via a syringe. After about 10 minutes, the reaction mixture becomes clear, followed by the formation of a cloudy precipitate of diiospropylurea. After stirring between 20° C. and 30° C. for one to four days, the reaction is terminated by pouring the reaction mixture slowly and with vigorous stirring into ten volumes of methanol. The polymer precipitates while the residual reagents remain dissolved in methanol, resulting in the formation of the clear supernatant.

The polymeric product is retrieved by filtration and washed with large amounts of methanol to remove any impurities. If desired, the polymeric products can be further purified by dissolving in methylene chloride (10% or 20% w/w) and reprecipitating in methanol. The polymeric product is then dried to constant weight under high vacuum.

In order to make polyarylates having free carboxylic acid groups in the pendant chains, it is not sufficient to simply use the above-described polymerization processes and include monomers having free carboxylic acid groups. This is because the free carboxylic acid groups would cross-react with the carbodiimide coupling reagents used in the above-described processes. Instead, the method described in U.S. Pat. No. 6,120,491, the disclosures of which are incorporated by reference herein, can be employed. In this method, a polyarylate is synthesized, e.g., by the processes described above, with the inclusion of a monomer having a protecting group on the pendant chain that can be selectively removed after the polyarylate is synthesized. This protecting group must be capable of being removed without significant degradation of the polymer backbone and without removal of ester groups from pendant chains at those positions where it is desired that free carboxylic acid groups not be present in the final polymer.

A preferred method uses benzyl esters as the protecting group. Thus, if it is desired to have a polyarylate with a certain percentage of free carboxylic acid groups, then one would produce an intermediate step polyarylate with that percentage of monomers having benzyl esters in their pendant chains. The benzyl esters are selectively removed by palladium-catalyzed hydrogenolysis in N,N-dimethylformamide (DMF) or similar solvents such as N,N-dimethylacetamide (DMA) and N-methylpyrrolidone (NMP) to form pendent carboxylic acid groups. Pure DMF, DMA, or NMP is necessary as the reaction solvent. The reaction medium must be anhydrous and the solvents have to be dried to ensure complete removal of all benzyl ester groups in the hydrogenolysis reaction. Essentially any palladium-based hydrogenolysis catalyst is suitable but, in preferred methods, the palladium catalyst is palladium on barium sulfate. A level of palladium on barium sulfate between about 5% and about 10% by weight is preferred. Preferred methods also use 1,4-cyclohexadiene, a transfer hydrogenolysis reagent, in combination with hydrogen gas as a hydrogen source. The polymer starting material having pendent benzyl carboxylate groups can be dissolved in dimethylformamide at a solution concentration (w/v %) between about 5% and about 50%, and preferably between about 10% and about 20%. For further details, U.S. Pat. No. 6,120,491 can be consulted.

The co-polymers of tyrosine-based polyarylates and poly (alkylene oxides) depicted in Formula 1 can be prepared by methods described in U.S. Pat. No. 6,048,521 and U.S. Pat. No. 6,120,491, the disclosures of which are incorporated by reference herein.

Preferred polyarylates have weight-average molecular weights above about 40-50 kd. A preferred weight-average molecular weight range is about 40 kd to about 400 kd; more preferably about 25 kd to about 150 kd; even more preferably about 50-100 kd. Molecular weights can be calculated from gel permeation chromatography (GPC) relative to polystyrene standards without further correction. The molecular weight of the polyarylate polymer used in the present invention is a factor that the skilled artisan will consider when developing a polyarylate/psychoactive drug combination for a particular use. In general, keeping all other factors constant, the higher the molecular weight of the polymer, the slower will be the release rate of the psychoactive drugs.

Systematic variations in polyarylate properties can be obtained by varying the nature of the pendant group attached to the C-terminus of the tyrosine-derived diphenol and the methylene groups in the dicarboxylic acid. One property that can be varied is the glass transition (Tg) temperature of the polyarylate polymer. This is exemplified by the approximately 1° C. increments in the glass transition temperature observed in the series of polyarylate polymers described in Brocchini et al., 1997, J. Amer. Chem. Soc. 119:4553-4554.

In general, keeping all other factors constant, the higher the Tg of the polymer, the slower will be the release rate of the psychoactive drug. Therefore, one can vary the Tg of the polyarylate polymers, and thus the release rate of the psychoactive drug, by adjusting the identity of the dicarboxylic acid and the pendant chain ester groups.

The polydispersity index (PDI) of the polyarylates should be in the range of 1.5 to 4, preferably 1.8 to 3. Manipulating the polydispersity provides another way to adjust the release rate of the psychoactive drug. Higher molecular weight polymers release psychoactive drugs more slowly than lower molecular weight polymers. Thus, a batch of a particular polymer with an average molecular weight of 80 kd and a PDI of 1.5 should release the psychoactive drugs more slowly than another batch of the same polymer with an average molecular of 80 kd but a PDI of 3, since the second batch is more polydisperse and thus has more lower molecular weight components than the first batch.

The tyrosine-derived diphenol monomers and corresponding tyrosine-derived polyarylates are biocompatible. The dicarboxylic acids generally are naturally occurring metabolites like adipic acid and succinic acid. Since the polyarylates contain an ester linkage in the backbone, they are biodegradable and their degradation products, tyrosine, desaminotyrosine, and the dicarboxylic acids, all have known toxicity profiles. The polyarylates produce significantly less acid during their degradation process than the PLGA family.

Several members of the polyarylates useful in the present invention were extensively tested in a variety of in vitro and in vivo assays and were found to exhibit excellent biocompatibility (Hooper et al., 1998, J. Biomed. Mat. Res. 41:443-454). In long-term in vivo studies, it has been determined that the degradation products of the polyarylates appear to be innocuous to surrounding tissue and promote ingrowth. In addition, surrounding tissue does not appear to exhibit inflammation in response to the polyarylate degradation products. Implants in sheep, rabbits, dogs, and rats have demonstrated minimal tissue reaction and no local or systemic toxicity.

Psychoactive Drugs

Psychoactive drugs are those that are useful for treating a neurological or psychological condition. Those conditions include, but are not limited to, psychosis, neurosis, anxiety, ataxia, vertigo, depression, and other psychogenic conditions. Many drugs in this class are targeted at conditions such as schizophrenia, acute mania, bipolar mania, psychotic agitation, bipolar maintenance, and other indications. One group of antipsychotic drugs, the Psychoactives, are broadly divided into two groups, the typical or first-generation antipsychotics and the atypical or second-generation antipsychotics. The typical antipsychotics are classified according to their chemical structure while the atypical antipsychotics are classified according to their pharmacological properties. These include serotonin-dopamine antagonists, multi-acting receptor-targeted psychoactives (MARTA, those targeting several systems), and dopamine partial agonists, which are often categorized as atypicals.

Atypical antipsychotics drugs are a group of drugs united by the fact that they work differently from the class of drugs terms typical antipsychotics. Most atypical antipsychotic drugs share a common attribute of working on serotonin receptors as well as dopamine receptors. One drug, amisulpride, does not have serotonergic activity. Instead it has some partial dopamine agonism. Another drug, aripiprazole, also displays some partial dopamine agonism, 5-$HT_{1A}$ partial agonism, and 5-$HT_{2A}$ antagonism.

In general, a wide variety of psychoactive drugs are suitable for use in the present invention. The choice of psychoactive drug may depend on such factors as: condition to be treated, the compatibility of the chemical nature (e.g., solubility, hydrophobicity) of the psychoactive drug with the chosen polyarylate, safety profile of the psychoactive drug, efficacy of the psychoactive drug, dose requirements of the psychoactive drug, cost of the psychoactive drug, etc.

Exemplary typical psychoactive drugs fall into three general chemical classes: butyrophenones; phenothiazines; and thioxanthenes. Exemplary typical psychoactive drugs include:

Chlorpromazine (LARGACTIL, THORAZINE);
Fluphenazine (PROLIXIN);
Haloperidol (HALDOL, SERENACE);
Molindone;
Thiothixene (NAVANE);
Thioridazine (MELLARIL);
Trifluoperazine (STELAZINE);
Loxapine (LOXAPAC, LOXITANE);
Perphenazine;
Prochlorperazine (COMPAZINE, BUCCASTEM, STEMETIL);
Pimozide (ORAP); and
Zuclopenthixol (CLOPIXOL).
Exemplary atypical psychoactive drugs include:
Amisulpride (SOLIAN);
Aripiprazole (ABILIFY);
Asenapine (SAPHRIS);
Clozapine (CLOZARIL, LEPONEX, FAZACLO, FROIDIR, DENZAPINE, ZAPONEX, KLOZAPOL, CLOPINE);
Iloperidone (FANAPT, FANAPTA, ZOMARIL);
Melperone (BURONIL, BURNIL, EUNERPAN);
Olanzapine (ZYPREXA, ZYPREXA ZYDIS, ZALASTA, ZOLAFREN, OLZAPIN, REXAPIN, SYMBYAX);
Paliperidone (INVEGA);
Perospirone (LULLAN);
Quetiapine (SEROQUEL, KETIPINOR);
Risperidone (RISPERDAL, RIDAL, SIZODON, RISCALIN, RISPOLEPT, BELIVON, RISPEN);
Sertindole (SERDOLECT, SERLECT);
Sulpiride (MERESA, SULPIRID, BOSNYL, DOGMATIL, EGLONYL, SULPIRYD);
Ziprasidone (GEODON, ZELDOX).

In a particular embodiment, the psychoactive drug used in the formulations of the invention is olanzapine. Olanzapine is a thienobenzodiazepine type atypical psychotropic agent. It is used to help manage symptoms of schizophrenia, the manic phase of manic depression, and other psychotic disorders. Olanzapine has a higher affinity for 5-$HT_2$ serotonin receptors than $D_2$ dopamine receptors. Like most atypical psychoactives, olanzapine has a lower affinity for histamine, cholinergic muscarinic and alpha adrenergic receptors.

Compositions of Matter Including Polyarylates and Psychoactive Drugs

The present invention provides combinations of polyarylates and psychoactive drugs that are useful for the sustained delivery of psychoactive drugs. The combination can take the form of a mixture or dispersion of the psychoactive drug in the polyarylate. The psychoactive drug can be physically admixed, dispersed, or embedded in the polymer by methods known in the art such as, e.g., dissolving the polyarylate and psychoactive drug together in an organic solvent and solvent casting a drug delivery implant from the common solution. Preferred organic solvents are chloroform, methylene chloride, tetrahydrofuran (THF), and ethyl formate/methanol. The polyarylate and the psychoactive drug generally form a homogeneous solid polymer matrix where the psychoactive drug is miscible in and evenly distributed throughout the polymer matrix.

In another method of making the polyarylate/psychoactive drug combination, dry mixtures of polyarylate polymer and psychoactive drug may be blended and then compression molded or extruded at an elevated temperature, e.g., 100-110° C., provided the psychoactive drug is stable at those temperatures for the duration of manufacture. In another method of formulating the polyarylate/psychoactive drug combination, dry mixtures of polyarylate polymer and psychoactive drug are milled to form powders. The milled powders can be sieved to obtain powders of desired particle size. The size of the particles can be controlled in order to produce desired rates of release of the psychoactive drug. In general, larger sized particles will lead to slower release rates than smaller sized particles. A preferred particle size is between about 50 to 100 microns.

A further method of making microparticles including a polyarylate and an psychoactive drug includes: (a) preparing a first phase, the first phase including an organic solvent in which an psychoactive drug and a polyarylate polymer are dissolved; (b) preparing a second phase, in which the second phase is an aqueous phase and the first phase is substantially immiscible in the second phase; (c) combining the first phase and the second phase to form an emulsion in which the first phase is discontinuous and the second phase is continuous; and (d) stirring the emulsion until the organic solvent in the first phase evaporates, such that microparticles including the polyarylate and the psychoactive drug are formed.

Mechanical agitation of the combined first and second phases or the addition of small drops of the first phase to the second phase can be used to form the emulsion. The temperature during the formation of the emulsion is not especially critical, but can influence the size and quality of the microparticles and the solubility of the psychoactive drug in the second phase. It is desirable to have as little of the psychoactive drug in the second phase as possible. It will be known to the skilled artisan that the temperature of the emulsion cannot be so high that the stability of the particular psychoactive drug being incorporated in the microparticles is adversely affected. For most psychoactive drugs and polyarylates, the temperature can be from about 20° C. to about 60° C.

As a modification of the above process, rather than stirring the emulsion until the organic solvent in the first phase evaporates, a quench solution can be added to remove the organic solvent, thus forming microparticles. In certain embodiments, the compositions are formulated such that the psychoactive drug is covalently bound to the polymer. In other embodiments, the composition is formulated such that the psychoactive drug and the polymer are combined in a non-covalent manner, i.e., the psychoactive drugs are not covalently bonded to the pendant carboxyl chain of the tyrosine-derived portion of the polyarylate.

A preferred formulation of the polyarylate/psychoactive drug composition of the present invention is microspheres or microparticles, in an aqueous solution for injection. Microparticles are solid particles, generally round, optionally smooth, made from a polyarylate polymer matrix and having a diameter of about 50 µm to about 750 µm. Microparticles can be made by grinding preformulated film as exemplified in Examples below or by mixing the psychoactive drug and the polymer in a solvent, drying and grinding the dried powder to produce microparticles of the desired size as exemplified in Examples below. Microspheres are solid particles, generally round, optionally smooth, made from a polyarylate polymer matrix and having a diameter of about 50 μm to about 750 μm. Microspheres are made by a standard oil-in-water emulsification methodology or similar method (see, e.g., Freiberg et al. (2004) Int. J. Pharm., 282(1-2) 1-8, "Polymer microspheres for controlled drug release"). The microspheres can be also be dried and ground into a powder to produce microspheres of a desired size.

The present invention includes pharmaceutical compositions including microparticles, in which the microparticles include a polyarylate polymer matrix in which an psychoactive drug is mixed, dispersed, or embedded. Preferably, the microparticles are biodegradable and biocompatible and have a size range of from about 25 microns to about 750 microns. Biocompatible refers to non-toxic to the mammalian body, and in particular, non-toxic to the human body. Biocompatible substances are pharmaceutically acceptable, non-carcinogenic, and are not prone to induce inflammation. Biodegradable refers to a substance that is able to be broken down to its constituent subunits in the mammalian body in a period of time of no more than 2 years, the exact time depending on the amount and nature of the biodegradable substance.

Several procedures are available to prepare microspheres. The simplest is the single emulsion method. In this method, the polymer and drug are dissolved in an organic solvent that is immiscible with water. The organic solution of polymer and drug is added to an aqueous solution containing 1-2% polyvinyl alcohol (surfactant/stabilizer). The mixture is stirred and the solvent allowed to evaporate, leading to the formation of microspheres or microparticles containing the drug embedded in the polymer. The particles faulted are collected by filtration or centrifugation, dried, and sieved to the desired size. This method works especially well when the drug to be incorporated has good solubility in the organic phase and limited solubility in the aqueous phase. Particle size can be controlled by the concentration (viscosity) of polymer solution, stirring speed, concentration of polyvinyl alcohol, and rate of evaporation.

Accordingly, the present invention provides a method of making microspheres including a polymer matrix formed by a polyarylate polymer in which an psychoactive drug is dispersed, dissolved, or embedded in the polyarylate polymer matrix in which the method includes: (a) dissolving the polyarylate polymer and the psychoactive drug in an organic solvent that is immiscible with water to form a polyarylate polymer/psychoactive drug solution; (b) adding the polyarylate polymer/psychoactive drug solution to an aqueous solution of 1-2% polyvinyl alcohol to form a mixture; (c) stirring the mixture until the organic solvent in the mixture evaporates; thereby forming microspheres including a polymer matrix formed by a polyarylate polymer in which a psychoactive drug is dispersed, dissolved, or embedded in the polyarylate polymer matrix.

The microsphere formulation may be stored dry as a powder in vials, suspended in a viscous, aqueous liquid or phosphate buffered saline (PBS), and injected through a 20-gauge or other needle at various sites.

Incorporation by Reference

References and citations to other documents, such as patents, patent applications, patent publications, journals, books, papers, web contents, have been made throughout this disclosure. All such documents are hereby incorporated herein by reference in their entirety for all purposes.

Equivalents

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Olanzapine (2-methyl-4-(4-methyl-1-piperazinyl)-10H-thieno[2, 3-b][1,5]benzodiazepine) is a yellow crystalline solid. The structure of olanzapine is shown below.

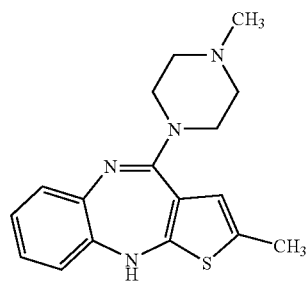 [SMILES: Cc1cc2c(s1)Nc1ccccc1N=C2N1CCN(C)CC1]

It is a highly lipophilic drug that is very soluble in chlorinated solvents, and virtually insoluble in water, making it an ideal candidate for microsphere (MS) preparation using oil in water techniques.

A representative structure of the tyrosine-derived polyarylate family and details of polyarylate structures are provided in Table 1.

TABLE 1

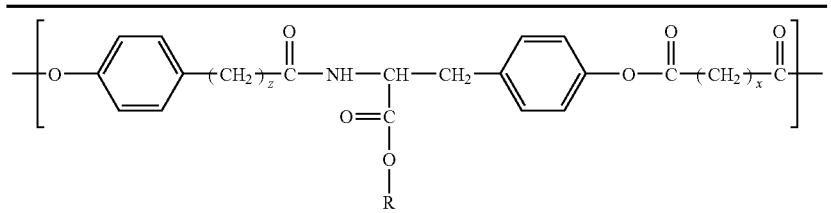

| Polymer | X | Z | R |
|---------|---|---|--------|
| 1       | 2 | 1 | Ethyl  |
| 2       | 2 | 0 | Methyl |

TABLE 1-continued $$\left[\!-\!O\!-\!\!\!\bigcirc\!\!\!-\!(CH_2)_{\overline{z}}\!-\!\!\overset{O}{\underset{\|}{C}}\!-\!NH\!-\!\underset{\underset{O}{\overset{|}{C}}=\!C}{\overset{|}{CH}}\!-\!CH_2\!-\!\!\!\bigcirc\!\!\!-\!O\!-\!\overset{O}{\underset{\|}{C}}\!-\!(CH_2)_{\overline{x}}\!\overset{O}{\underset{\|}{C}}\!-\!\right]$$

| Polymer | X | Z | R |
|---|---|---|---|
| 3 | 4 | 1 | Benzyl |
| 4 | 2 | 1 | Ethyl/H (9/1) |
| 5 | 4 | 1 | Hexyl/H (9/1) |

Example 1

Materials and Methods

Polymer Synthesis

Tyrosine derived polyarylates were prepared by a carbodimide mediated coupling reaction (U.S. Pat. No. 6,120, 491, Biodegradable, anionic polymers derived from the amino acid L-tyrosine). Briefly, equimolar amounts of a diacid and a diol were condensed in methylene chloride using diisopropyl carbodimide as the coupling agent and a mixture of dimethylaminopyridine and paratoluenesulfonic acid. The polymer was isolated by repeated precipitations into 2-propanol.

Polymer Characterization

The polymers were characterized by $^1H$ NMR and $^{13}C$ NMR (nuclear magnetic resonance) for structure confirmation, GPC (gel permeation chromatography) for molecular weight, TGA (thermal gravimetric analysis) for decomposition temperature and DSC (differential scanning calorimetry) for glass transition temperature.

Microsphere Preparation and Characterization

Microspheres were prepared by an oil/water emulsion technique using polyvinyl alcohol as the surfactants (Freiberg S., X X Zhu, Polymer microspheres for controlled drug release. (2004) Int. J. Pharm., 282(1-2) 1-8). Particles of the desired size were collected using different sized sieves. The size and physical appearance of the particles were assessed by scanning electron microscopy (SEM). Drug/polymer interactions were evaluated by DSC.

Drug Loading

Drug load was determined by quantitative HPLC analysis of microspheres. Briefly, 10 mg of microspheres were dissolved in 1 mL DMSO. 20 mL methanol was added with vigorous shaking on a vortex mixer to precipitate the polymer. The precipitate was removed by filtration and the clear supernatant was analyzed by HPLC. The amount of drug was calculated from a previously constructed calibration curve. Loading for different formulations varied from 11.5 to 14.5%.

Drug Release Studies

The drug release studies were conducted in 20 mL scintillation vials at 37° C. The amount of released drug was assessed by analyzing the PBS release medium at different time points using HPLC. The kinetics of drug release was obtained by plotting the cumulative drug released against time.

High Performance Liquid Chromatography-HPLC

Olanzapine was assayed by HPLC using a Perkin Elmer 200 series instrument, UV detection at 270 rim and Turbochrom Software. A Brown Lee C18 30×4 6 mm 110 A column was operated at 1 mL/min in a gradient of water and methanol.

Polymer Molecular Weight

Molecular weight (MW) of polymers was determined on a GPC system consisting of a Waters 2690 separations module, Waters model 410 differential refractometer and Empower Software. Three PL-gel GPC columns ($10^5$ Å, $10^3$ Å, 50 Å pore size) were operated in series at a flow rate of 0.8 ml/min in DMF with 0.1% Trifluoroacetic acid (TFA). Molecular weights were calculated relative to PEG standards (Polymer Laboratories, Ltd.) without further correction. The MW the polymers was between 50,000 to 100,000 Daltons.

Example 2

Micropshere (MS) Characterization

Smooth spherical particles were obtained from several members of this polymer family (A-polymer 1, B-polymer 2, C-polymer 3) bar=100 μm (FIG. 1).

Figure 2:
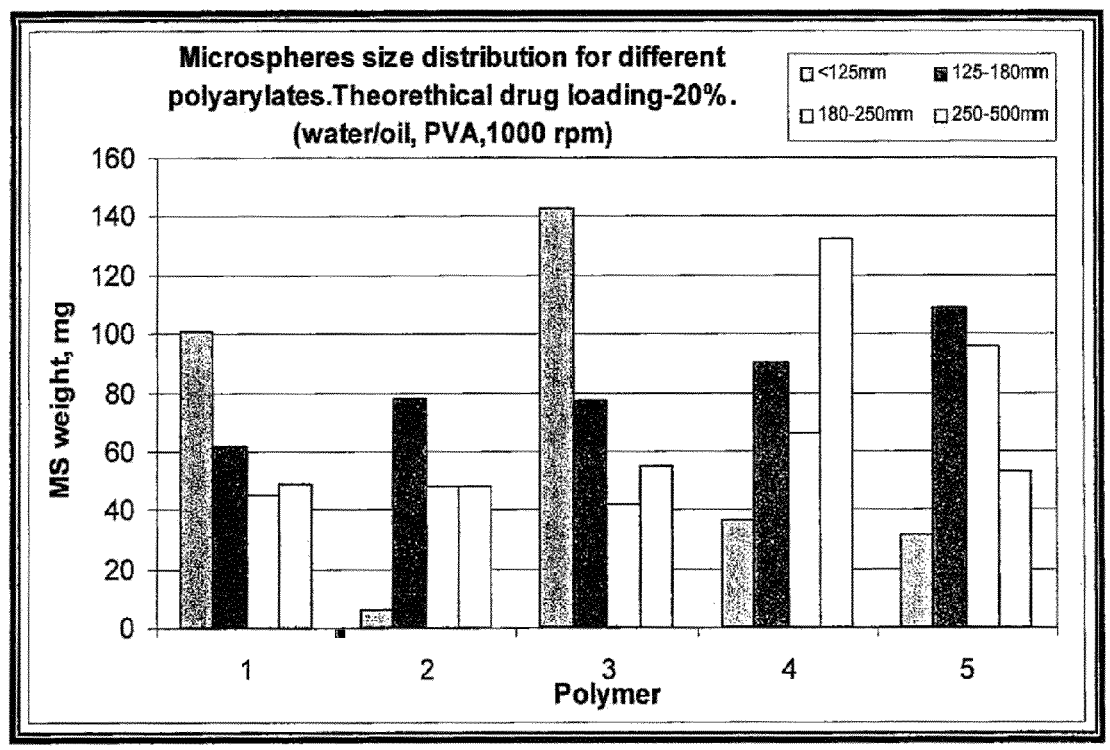
FIG. 2 is a bar graph showing microsphere size distribution for different polyarylates.
Figure 3:
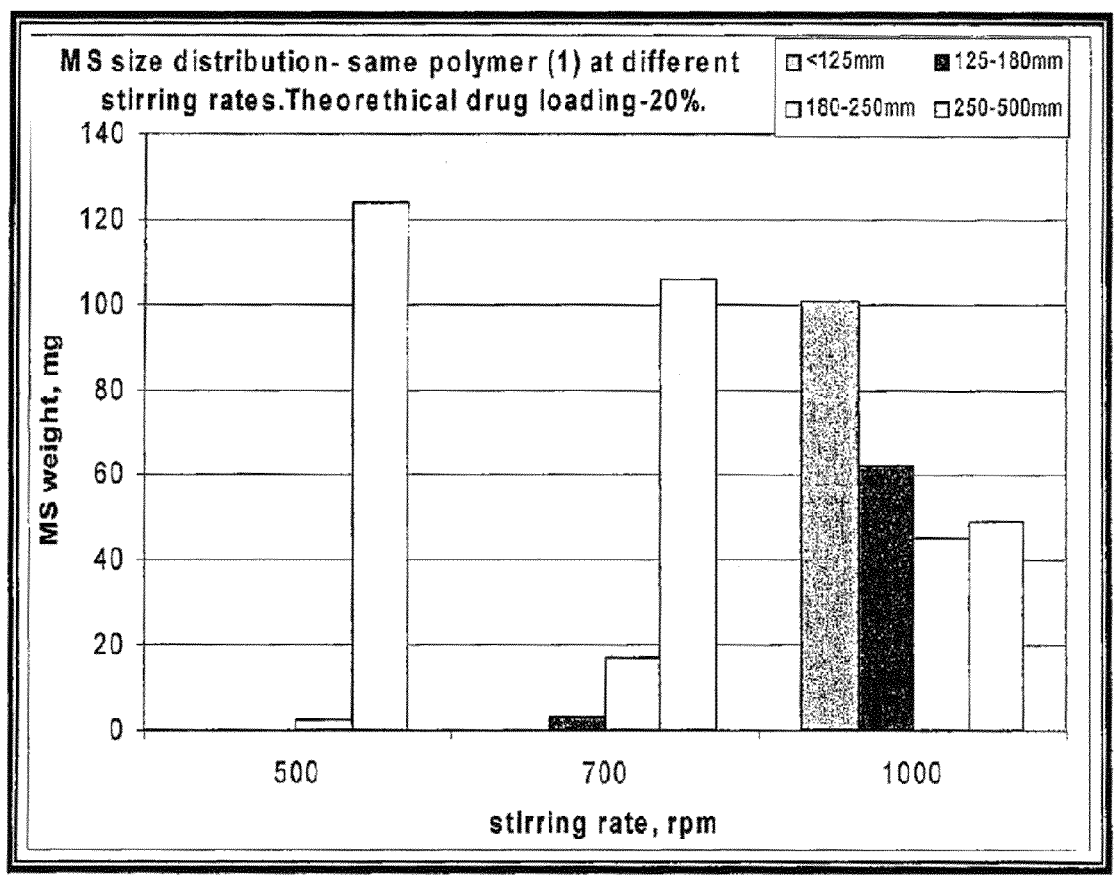
FIG. 3 is a bar graph showing microsphere polymer size distribution.
Figure 4:
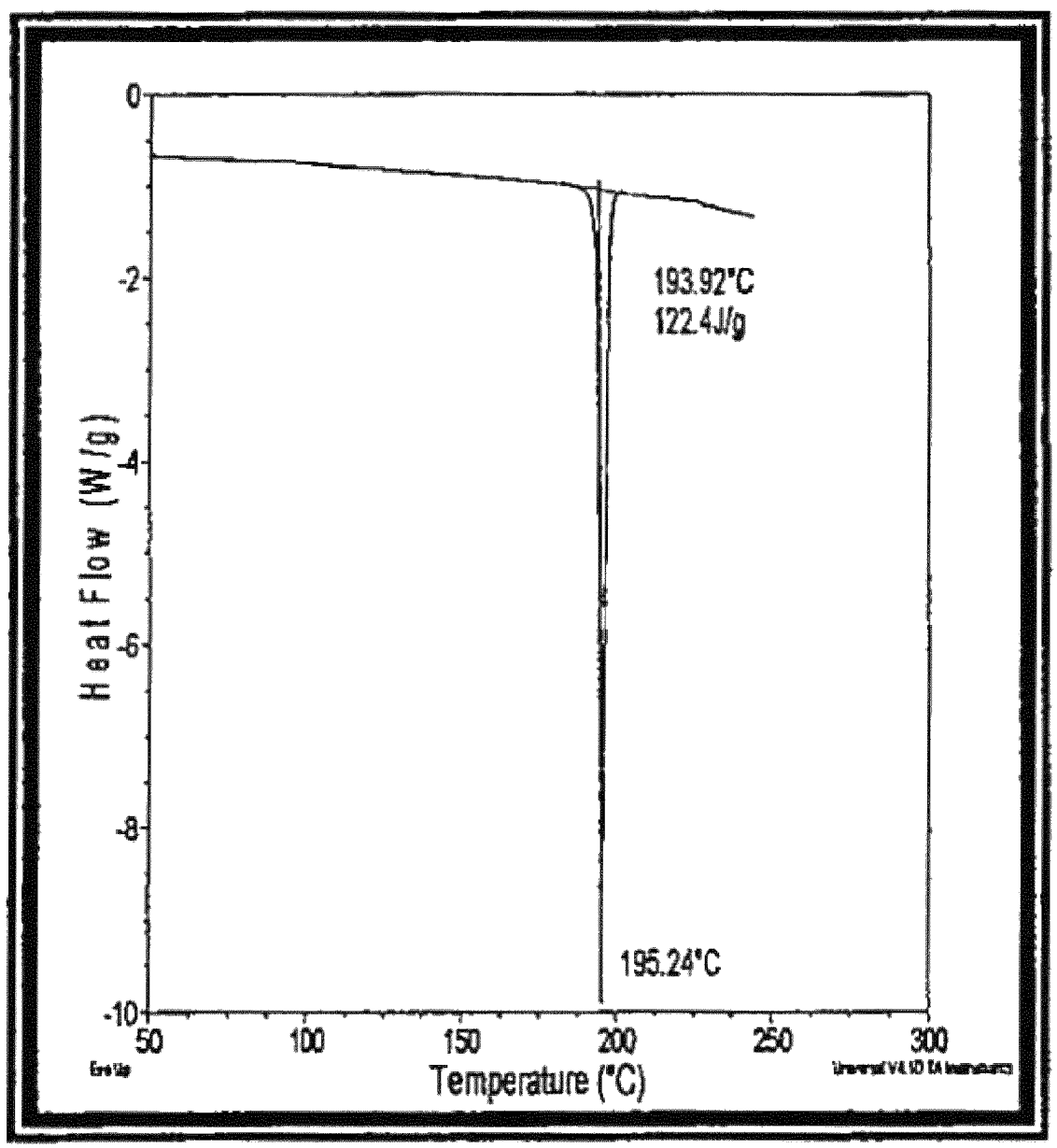
FIG. 4 is a graph showing the melting point of pure olanzapine.
Figure 5:
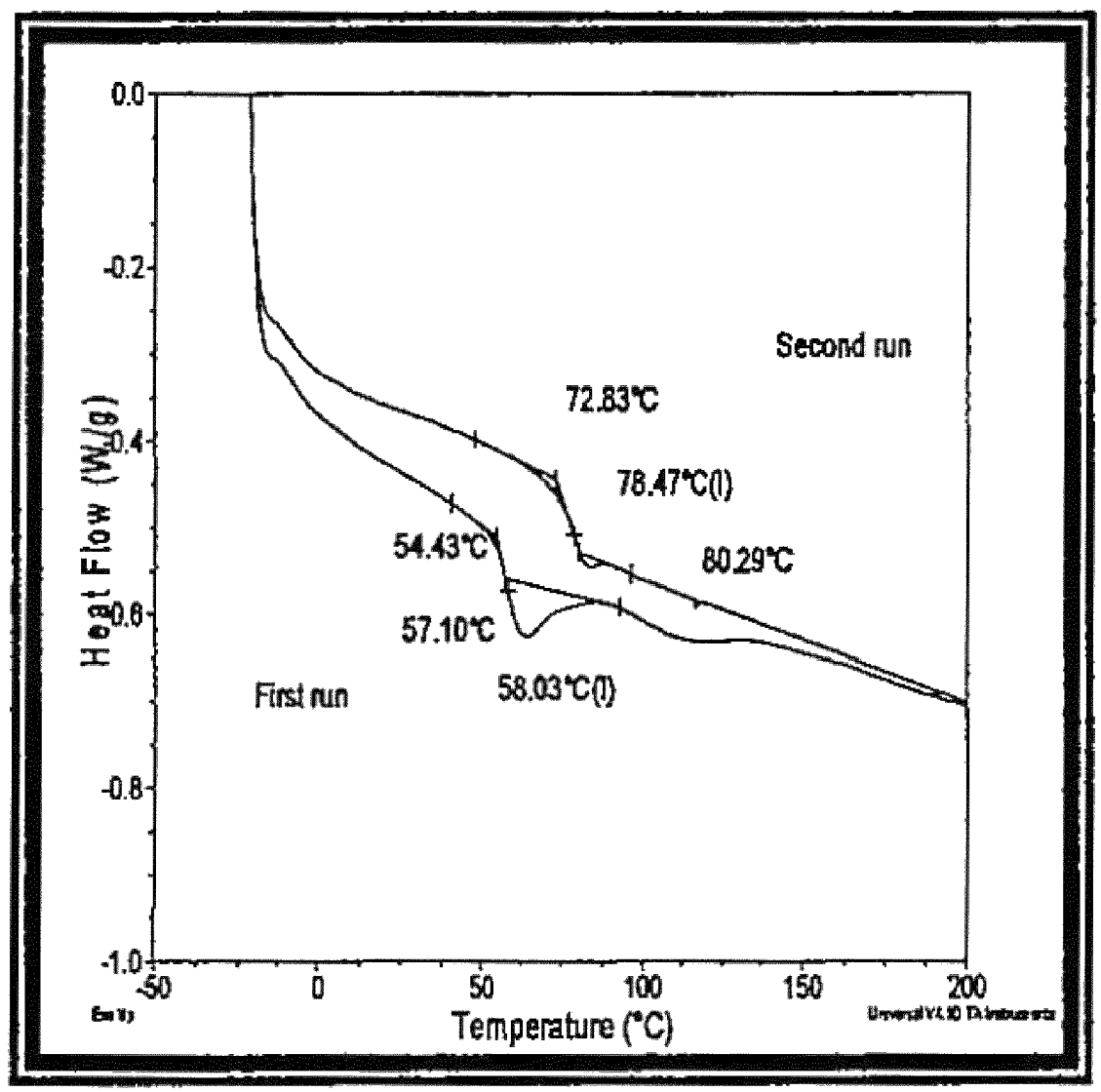
FIG. 5 is a graph showing the miscibility of olanzapine with polymer matrix.

FIG. 2 shows the particle size distribution obtained for a set of 5 polyarylates under the same process conditions, and the effect of stirring rate on particle size distribution of microspheres from the same polymer. FIG. 3 shows microsphere size distribution depends on nature of the polymer and stirring rate. All 5 samples (different polymers) were analyzed by DSC and did not show any phase separation or free drug. Pure olanzapine has a melting point of 195° C. (FIG. 4). As is shown on the DSC trace, there is no free drug signal and Tg (glass transition temperature) in both first and second runs is lower than pure polymer Tg (FIG. 5). This is an indication that drug is fully miscible with polymer matrix.

Example 3

Release Data

Figure 6:
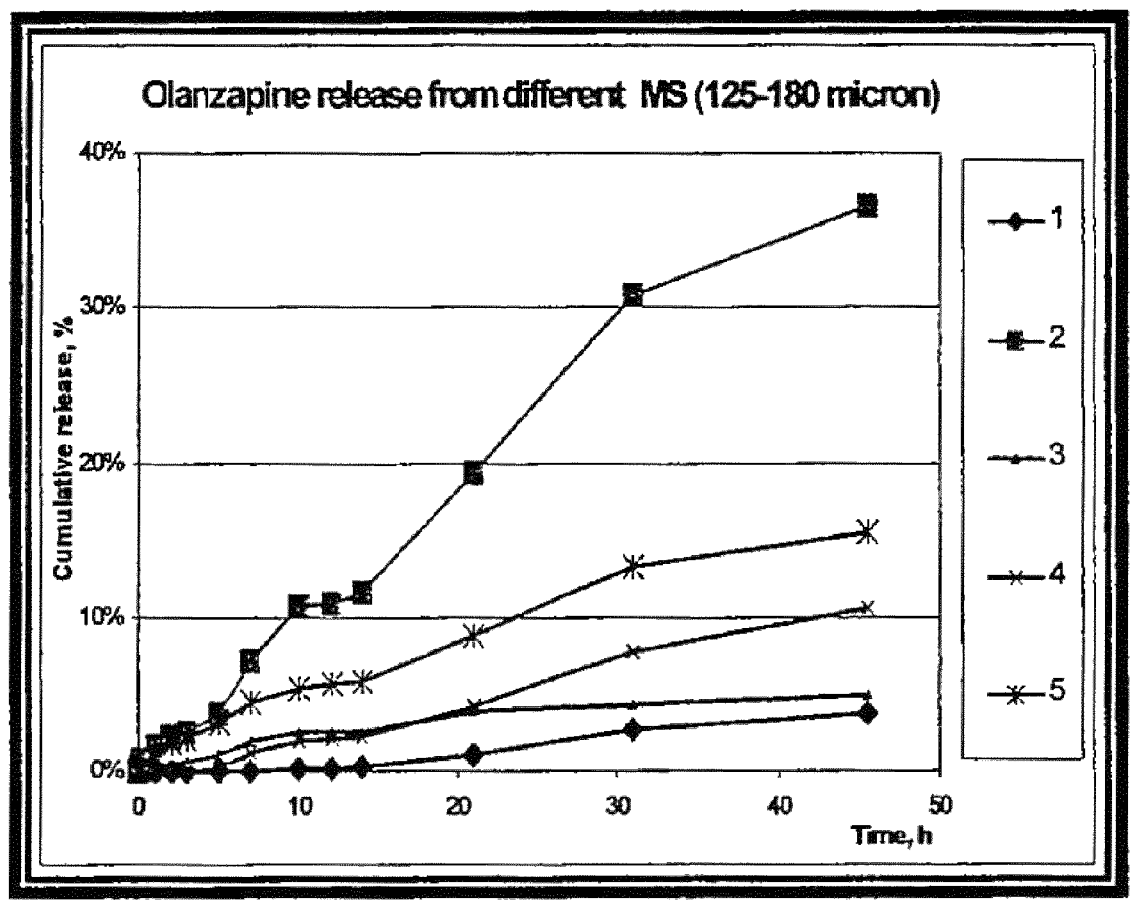
FIG. 6 is a graph showing olanzapine release from different sized microspheres (125-180 micron).
Figure 7:
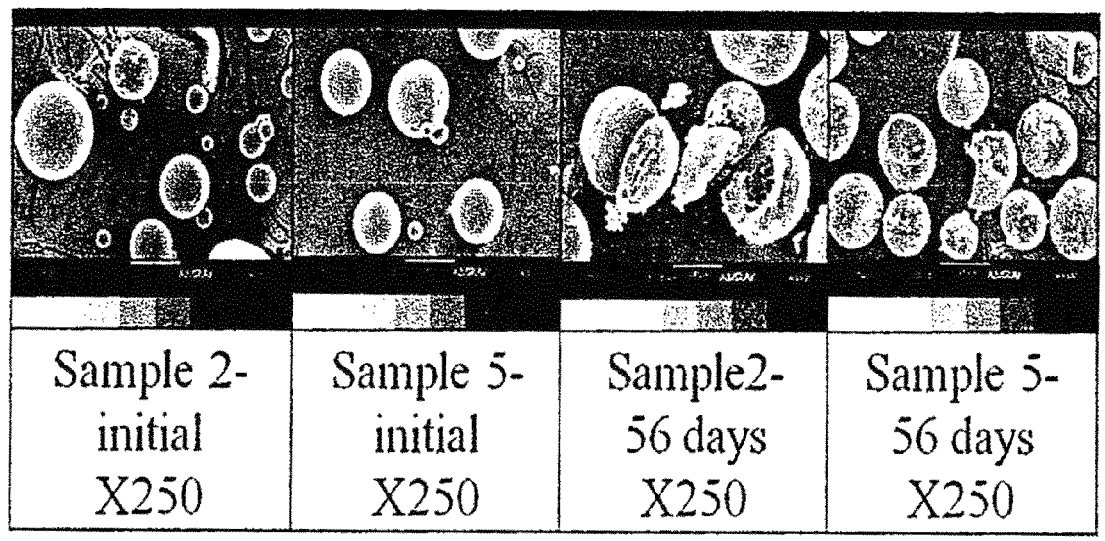
FIG. 7 is a set of SEM images of miscrospheres at an initial point in time and after 56 days of incubation.

Olanzapine release data from polyesteramide MS (125-180 mm) are shown in FIG. 6 below. There is no burst and olanzapine is slowly released for up to 45 days at different rates depending on the polymer used. FIG. 7 shows SEM images of initial MS and after 56 days of incubation, demonstrating that a bulk erosion mechanism prevails during polymer degradation. The MW data in Table 2 shows that the polymers degrade rapidly and less than 10% of MW remains after 2 months.

TABLE 2

| Sample | Initial Mw, kDa | 31 day | 52 days |
|---|---|---|---|
| 1 | 84.8 | 3.7 | 3.6 |
| 2 | 17.0 | 2.4 | 3.0 |
| 3 | 20.7 | 4.0 | 2.7 |
| 4 | 22.0 | 4.0 | 3.1 |
| 5 | 73.7 | 10.5 | 6.4 |

Figure 8:
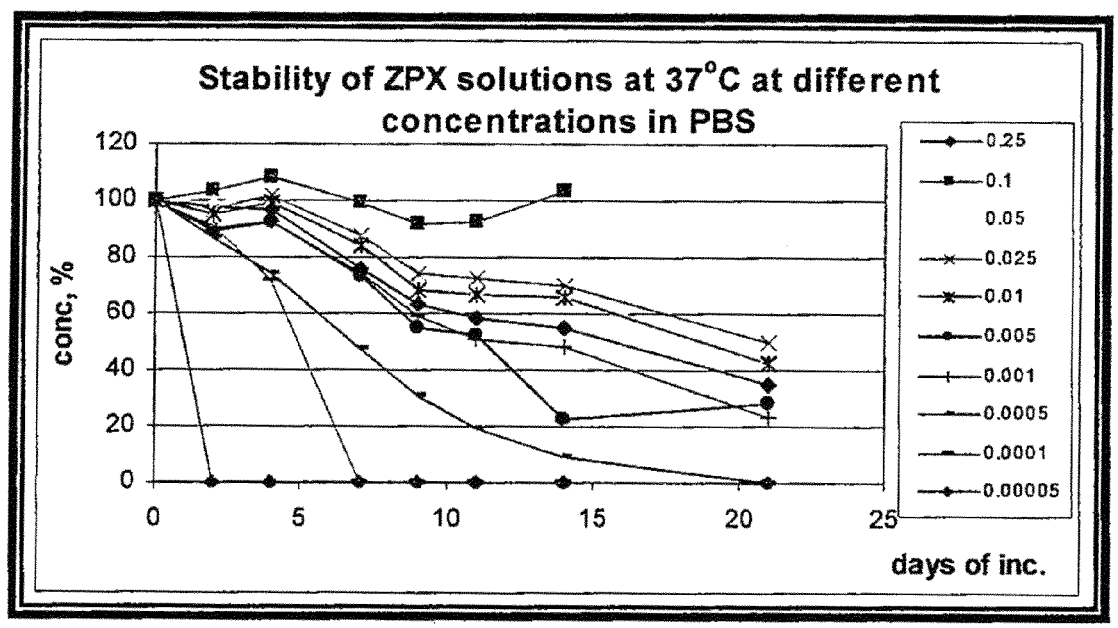
FIG. 8 is a graph showing stability of olanzapine at 37° C. at different concentrations in PBS.

Residual loading analysis showed that very little drug was left in the microspheres at the end of release (Table 3). Significant amount of olanzapine was not accounted for (Table 3). Additional experiments were performed to evaluate stability of olanzapine in PBS at 37° C. (FIG. 8). Results showed that olanzapine showed some unstable at 37° C. especially at low concentrations (FIG. 8). A 0.1% solution was surprisingly very stable—at least for first 14 days.

TABLE 3

| MS sample | Loading, % | % released | % residual | % lost |
|---|---|---|---|---|
| 1 | 12.55 | 4 | 10 | 86 |
| 2 | 14.32 | 37 | 4 | 59 |
| 3 | 14.67 | 5 | 26 | 69 |
| 4 | 11.50 | 11 | 15 | 74 |
| 5 | 11.77 | 15 | 16 | 69 |

Data show that polyarylates are suitable polymers for development of an olanzapine sustained release system with 45 days of drug elution.

What is claimed is:

1. A sustained-release formulation comprising a tyrosine-derived polyarylate having at least one p(DT-succinate) group and a psychoactive drug physically admixed, dissolved, dispersed, or embedded within said tyrosine-derived polyarylate, and wherein said tyrosine-derived polyarylate and said psychoactive drug form a homogeneous solid matrix, and wherein said formulation provides a burst-free, sustained release of said psychoactive drug.

2. The formulation according to claim 1, wherein when measured in vitro under physiological conditions at 37° C., amounts are such that the formulation releases the psychoactive for at least 1 to 5 days.

3. The formulation of claims 2, wherein the physiological conditions are in phosphate buffered saline (PBS).

4. The formulation according to claim 1, wherein the psychoactive drug is an atypical psychoactive drug.

5. The formulation according to claim 4, wherein the atypical psychoactive drug is olanzapine.

6. The formulation according to claim 1, wherein the formulation is prepared as a microparticle or a microsphere.

7. The formulation according to claim 1, wherein the tyrosine-derived polyarylate is a poly(DT-DTE succinate) or a poly(DTE succinate), wherein, DT, when present ranges from about 5% to about 50%, from about 5% to about 30%, from about 10% to about 20% of the polyarylate or is about 5%, 10%, 15%, 20%, 25% or 30% of said polyarylate.

8. The formulation according to claim 1, wherein the formulation comprises an amount of psychoactive drug ranging from about 10% to about 40% by weight.

9. A sustained-release formulation comprising a tyrosine-derived polyarylate and a psychoactive drug physically admixed, dissolved, dispersed, or embedded within said tyrosine-derived polyarylate, and wherein said tyrosine-derived polyarylate and said psychoactive drug form a homogeneous solid matrix, and wherein said formulation is prepared as a solvent-cast film or a solvent-free film.

10. The formulation according to claim 9, wherein when measured in vitro under physiological conditions at 37° C., amounts are such that the formulation releases the psychoactive for at least 1 to 5 days.

11. The formulation of claim 8, wherein the physiological conditions are in phosphate buffered saline (PBS).

12. The formulation according to claim 9, wherein the psychoactive drug is an atypical psychoactive drug.

13. The formulation according to claim 12, wherein the atypical psychoactive drug is olanzapine.

14. The formulation according to claim 9, wherein the psychoactive drug is olanzapine.

15. The formulation according to claim 9, wherein the formulation is prepared as a microparticle or a microsphere.

16. The formulation according to claim 9, wherein the formulation comprises an amount of psychoactive drug ranging from about 10% to about 40% by weight.

17. A burst-free, sustained-release microsphere or microparticle comprising a tyrosine-derived polyarylate having at least one p(DT-succinate) group and a psychoactive drug.

18. The microsphere or microparticle according to claim 17, wherein when measured in vitro under physiological conditions at 37° C., amounts are such that the formulation releases the psychoactive for at least 1 to 5 days.

19. The microsphere or microparticle of claims 18, wherein the physiological conditions are in phosphate buffered saline (PBS).

20. The microsphere or microparticle according to claim 17, wherein the psychoactive drug is an atypical psychoactive drug.

21. The microsphere or microparticle according to claim 17, wherein the atypical psychoactive drug is olanzapine.

22. The microsphere or microparticle according to claim 17, wherein the formulation comprises an amount of psychoactive drug ranging from about 10% to about 40% by weight.

23. The formulation of claim 1, wherein said tyrosine-derived polyarylate is comprised of a mixture of p(DTE-succinate) and p(DT-succinate) monomers.

24. The formulation of claim 1, wherein said formulation is prepared as a solvent-cast film or a solvent-free film.

25. The formulation of claim 9, wherein said said tyrosine-derived polyarylate is comprised of a mixture of p(DTE-succinate) and p(DT-succinate) monomers.

* * * * *